US00PP33760P2

(12) United States Plant Patent
Ramirez et al.

(10) Patent No.: US PP33,760 P2
(45) Date of Patent: Dec. 21, 2021

(54) STRAWBERRY PLANT NAMED 'PEP-12.6010'

(50) Latin Name: ***Fragaria* x *ananassa***
Varietal Denomination: PEP-12.6010

(71) Applicant: PLANT SCIENCES, INC., Watsonville, CA (US)

(72) Inventors: Cesar U. Ramirez, Scotts Valley, CA (US); Stephen M. Ackerman, Salinas, CA (US); Michael D. Nelson, Watsonville, CA (US)

(73) Assignee: Plant Sciences, Inc., Watsonville, CA (US)

( * ) Notice: Subject to any disclaimer, the term of this patent is extended or adjusted under 35 U.S.C. 154(b) by 0 days.

(21) Appl. No.: 17/344,619

(22) Filed: Jun. 10, 2021

Related U.S. Application Data

(60) Provisional application No. 63/041,601, filed on Jun. 19, 2020.

(51) Int. Cl.
*A01H 6/74* (2018.01)
*A01H 5/08* (2018.01)

(52) U.S. Cl.
USPC ..... Plt./209

(58) Field of Classification Search
USPC ..... Plt./209
See application file for complete search history.

*Primary Examiner* — Annette H Para
(74) *Attorney, Agent, or Firm* — Foley & Lardner LLP

(57) ABSTRACT

This invention relates to a new and distinct variety of strawberry plant named 'PEP-12.6010'. This new strawberry plant named 'PEP-12.6010' is primarily adapted to the growing conditions of the central coast of California, and is primarily characterized by its red fruit color, large fruit size, and conical fruit shape, with very strong gloss; good fruit flavor, medium fruit flesh firmness, with seeds held level with the surface; medium to large plant size, semi-upright in habit, with medium density; medium green foliage color, and small to medium foliage size; fruiting trusses typically held level with the plant, with medium pubescence; and resistance to *Fusarium* wilt.

5 Drawing Sheets

Latin name of the genus and species of the plant claimed: *Fragaria* x *ananassa.*

Variety denomination: 'PEP-12.6010'.

BACKGROUND OF THE INVENTION

The present invention relates to a new and distinct strawberry variety named 'PEP-12.6010'. This new variety is a result of a controlled cross made in 2012 in an ongoing breeding program between strawberry variety designated 'PE-6.2036' (U.S. Plant Pat.No. 26,209) as the seed (female) parent, and strawberry variety designated 'Triumph' (U.S. Plant Pat. No. 24,950) as the pollen (male) parent. The variety is botanically known as *Fragaria* x *ananassa.*

The seedling resulting from the aforementioned cross was selected from a controlled breeding plot in Ventura County, Calif. in the fall of 2014. After its selection, the new variety was asexually propagated by stolons in San Joaquin County, Calif. The new variety was tested extensively over the next several years in fruiting fields in Ventura County, Calif. This propagation has demonstrated that the combination of traits disclosed herein as characterizing the new variety are fixed and remain true-to-type through successive generations of asexual reproduction.

BRIEF SUMMARY OF THE INVENTION

'PEP-12.6010' is primarily adapted to the climate and growing conditions of the central coast of California. The nearby Pacific Ocean provides the humidity and moderate temperatures needed to produce a strong, vigorous plant and maintain fruit quality during the fall production months.

The following traits have been repeatedly observed and are determined to be unique characteristics of 'PEP-12.6010', which in combination distinguish this strawberry plant as a new and distinct variety:

1. Fruit is red in color, large in size, and conical in shape, with very strong gloss;
2. Fruit has good flavor, medium flesh firmness, with seeds held level with the surface;
3. Plant is medium to large in size, semi-upright in habit, with medium density;
4. Foliage is medium green in color, and ranges from small to medium in size;
5. Fruiting trusses are typically held level with the plant, with medium pubescence; and
6. Resistance to *Fusarium* wilt.

The strawberry variety that is believed to be most closely related to the new variety 'PEP-12.6010' is 'Portola' (U.S. Plant Pat. No. 20,552). In side-by-side comparisons to the similar strawberry variety 'Portola', 'PEP-12.6010' differs by the following combination of characteristics as described in Table 1.

TABLE 1

| Characteristic | 'PEP-12.6010' | 'Portola' (U.S. Plant Pat. No. 20,552) |
|---|---|---|
| Fruit: color | Red | Orange red |
| Fruit: insertion of achenes | Level with surface | Below surface |
| Fruit: flesh firmness | Medium | Very firm |
| Fruit: flavor | Good | Poor |
| Disease: | Moderate | Susceptible |

TABLE 1-continued

| Characteristic | 'PEP-12.6010' | 'Portola' (U.S. Plant Pat. No. 20,552) |
|---|---|---|
| Macrophomina wilt | | |
| Plant: color | Medium green | Light green |
| Plant: vigor | Medium to large | Very large |

For identification, a series of molecular markers have been determined for this new variety.

'PEP-12.6010' differs from its parents, 'PE-6.2036' and 'Triumph' by the following combination of characteristics as described in Tables 2 and 3.

TABLE 2

| Characteristic | 'PEP-12.6010' | 'PE-6.2036' (U.S. Plant Pat. No. 26,209) |
|---|---|---|
| Fruit: shape | Conical | Cordate |
| Fruit: flavor | Good | Excellent |
| Pedicel: pubescence | Medium | Weak |
| Disease: Fusarium wilt | Resistant | Susceptible |
| Plant: color | Medium green | Ranges from medium to dark green |

TABLE 3

| Characteristic | 'PEP-12.6010' | 'Triumph' (U.S. Plant Pat. No. 24,950) |
|---|---|---|
| Fruit: size | Large | Medium |
| Pedicel: pubescence | Medium | Strong |
| Fruiting truss: position relative to foliage | Level with | Ranges from beneath to level with |
| Fruiting truss: length | Medium | Ranges from medium to long |
| Maturing season | Medium | Early |

BRIEF DESCRIPTIONS OF THE DRAWINGS

The accompanying color photographs illustrate the overall appearance of typical specimens of the new strawberry variety 'PEP-12.6010' at various stages of development, as true as it is reasonably possible with color reproductions of this type. Color in the photographs may differ slightly from the color value cited in the botanical descriptions which accurately describe the color of 'PEP-12.6010'. The depicted plant and plant parts of the new strawberry variety 'PEP-12.6010' are approximately three to four months old. The photographs were taken in Ventura County, Calif.

DETAILED BOTANICAL DESCRIPTION

Figure 1:
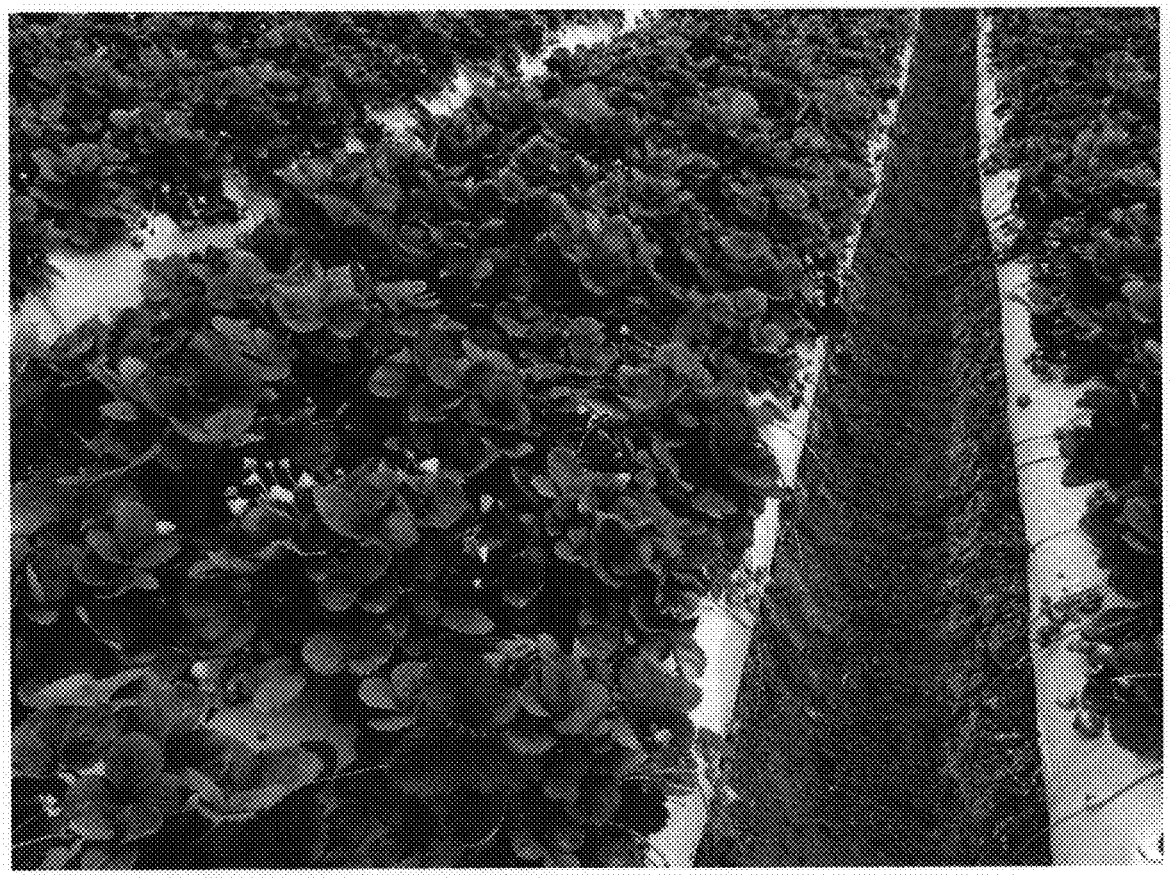
FIG. 1 shows fruiting field characteristics of 'PEP-12.6010', taken in the month of November 2020.
Figure 2:
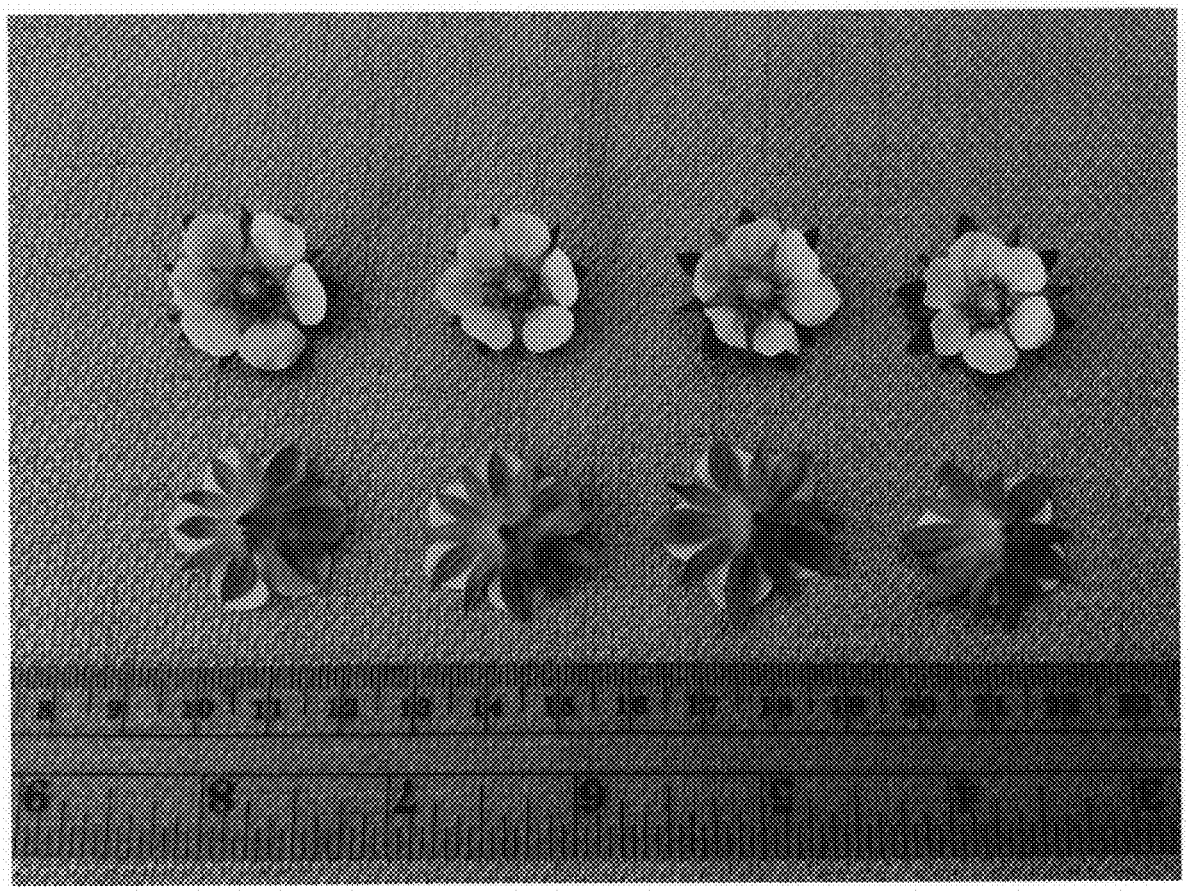
FIG. 2 shows upper and lower surfaces of flower and flower parts of 'PEP-12.6010', taken in the month of November 2020.
Figure 3:
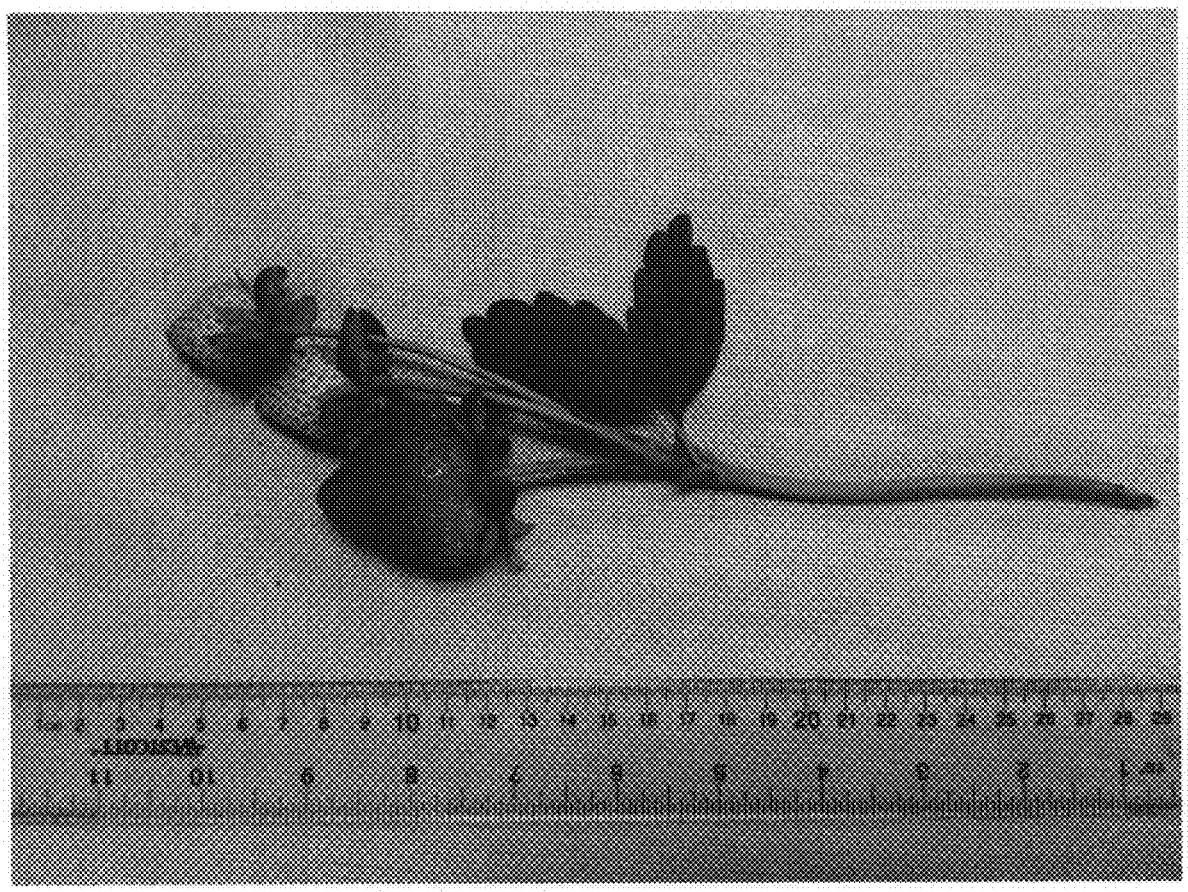
FIG. 3 shows typical fruiting truss and truss parts of 'PEP-12.6010', taken in the month of November 2020.
Figure 4:
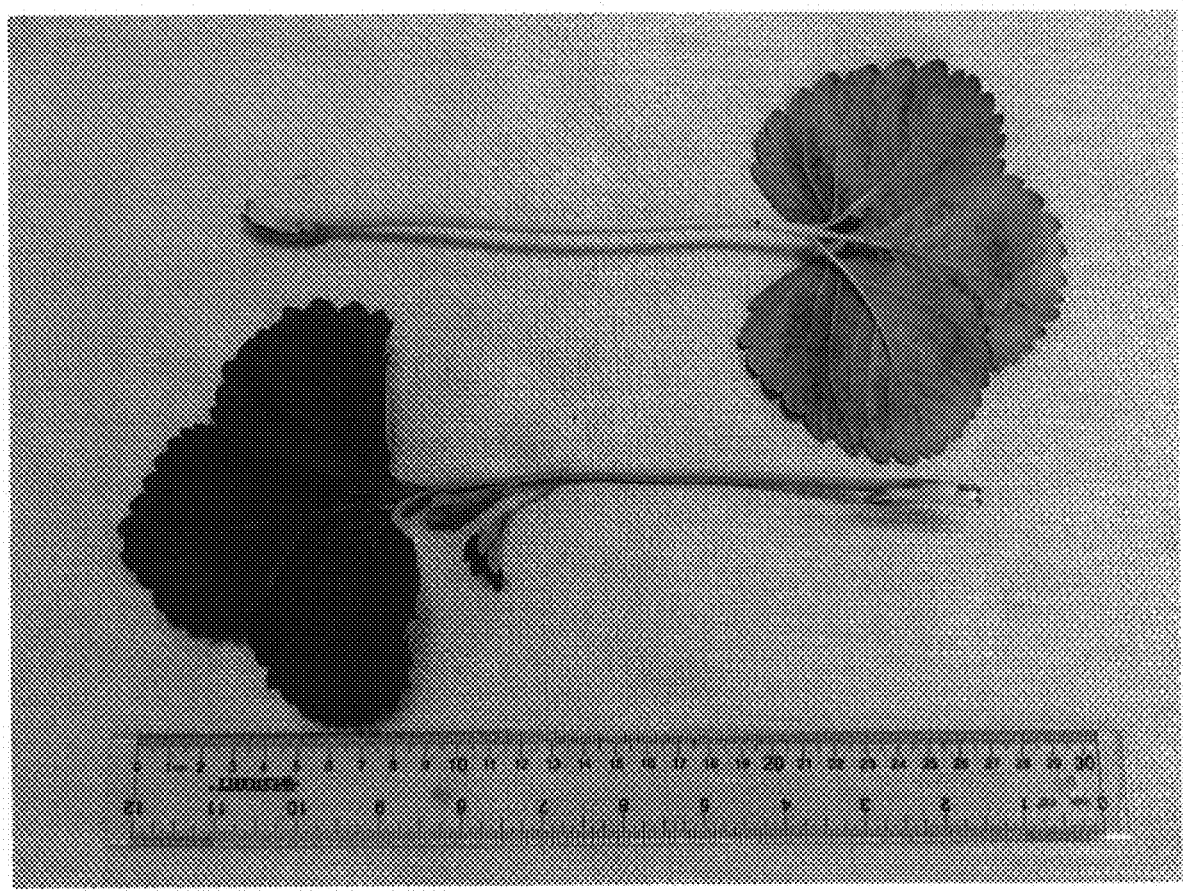
FIG. 4 shows upper and lower surfaces of leaf and leaf parts of 'PEP-12.6010', taken in the month of November 2020.
Figure 5:
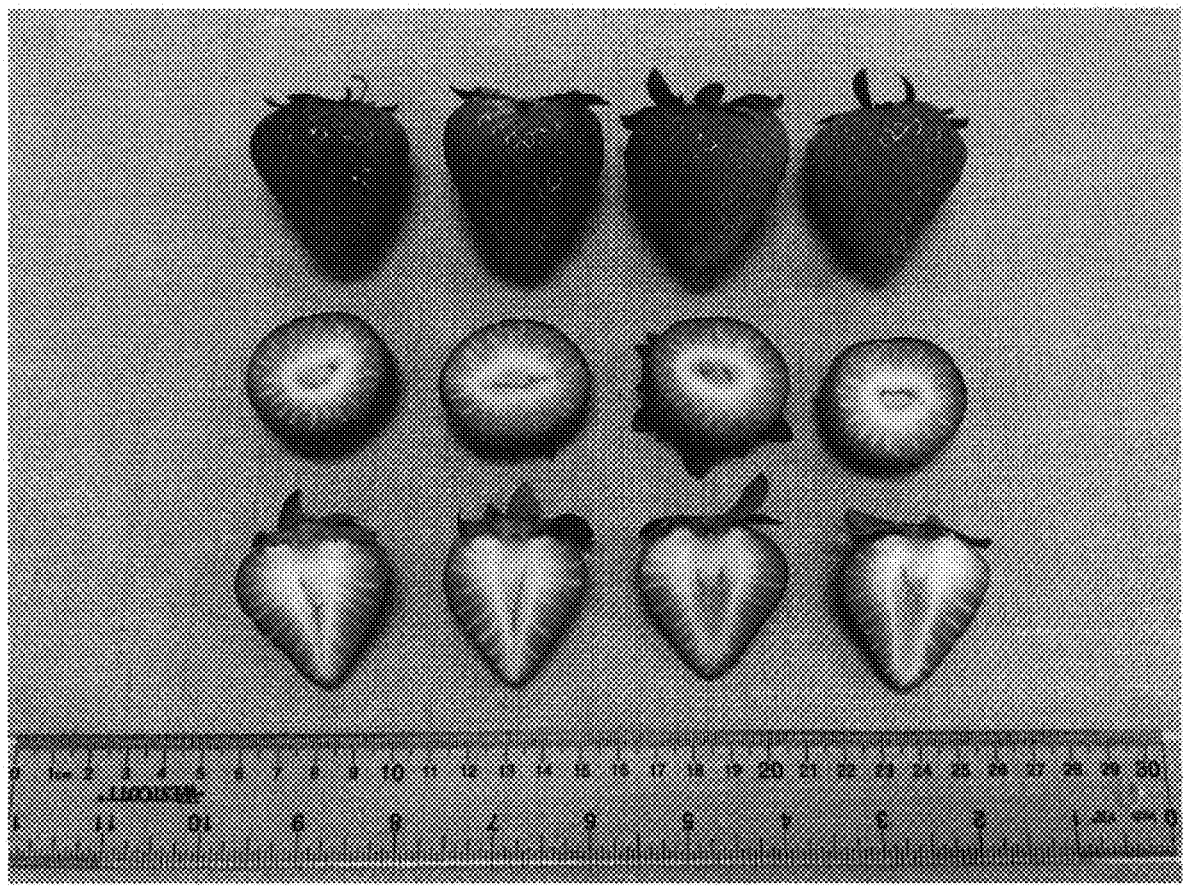
FIG. 5 shows internal and external mature fruit characteristics of 'PEP-12.6010', taken in the month of November 2020.

The new variety 'PEP-12.6010' has not been observed under all possible environmental conditions. The characteristics of the new variety 'PEP-12.6010' may vary in detail, depending upon variations in environmental factors, including weather (temperature, humidity and light intensity), day length, soil type and location. In addition, the characteristics of any parental variety or comparison variety included in Tables 1, 2 and 3 of the present invention may vary in detail, depending upon variations in environmental factors, including weather (temperature, humidity and light intensity), day length, soil type and location.

The aforementioned photographs, together with the following description of the new variety 'PEP-12.6010', unless otherwise noted, are based on observations taken during the 2020 growing season in Ventura County, Calif. These measurements and ratings were taken from plants of 'PEP-12.6010' dug from a low-elevation nursery located in San Joaquin County, Calif. in January 2020 and planted approximately six months later in Ventura County, Calif. The approximate age of the observed plants is four months. Yield observations including average weight and marketable yield, along with fruit quality characteristics including soluble solids, are averaged from five years of data collected from the 2016 through 2020 growing seasons. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London (2007).

The following characteristics describe fruit, plant, stolon, foliage, fruiting truss, flower, reproductive organs and pest and disease characteristics of the new strawberry 'PEP-12.6010'.

Fruit characteristics:

*Color of mature fruit.*—RHS 45A (red).
*Color of internal flesh (excluding core).*—RHS 44A (orange red).
*Color of core.*—RHS 44D (light red).
*Average length (cm).*—4.0.
*Average width (cm).*—3.8.
*Size.*—Large.
*Average length/width ratio.*—1.05 (as long as broad).
*Hollow center average length (mm).*—20.2.
*Hollow center average width (mm).*—4.2.
*Hollow center expression.*—Weak.
*Season average weight (gm).*—25.9.
*Marketable yield season (gm/plant).*—424.
*Predominant shape.*—Conical.
*Difference in shape between primary and secondary fruit.*—Slight.
*Band without achenes.*—Absent or very narrow.
*Evenness of surface.*—Even or very slightly uneven.
*Evenness of color.*—Even or very slightly uneven.
*Glossiness.*—Strong.
*Insertion of achenes.*—Level with surface.
*Average calyx diameter (cm).*—4.1.
*Position of calyx attachment.*—Inserted.
*Attitude of sepals.*—Outward.
*Size of calyx in relation to fruit diameter.*—Slightly larger.
*Adherence of calyx (when fully ripe).*—Strong.
*Firmness of flesh.*—Medium.
*Keeping quality.*—Good.
*Post-harvest fruit longevity (at 1 to 3 degrees Celsius).*—5 to 7 days.
*Fruit market.*—Fresh.

*Distribution of red color of the flesh.*—Marginal and central.
*Flavor.*—Good.
*Soluble solids (% Brix).*—8.2.
*Achene color, shaded side.*—RHS 160A (greyed yellow group).
*Achene color, sun-exposed side.*—RHS 185B (greyed purple group).
*Achene average length (mm).*—1.4.
*Achene average width (mm).*—1.0.
*Achene average weight (mg).*—0.6.
*Achene average quantity per berry.*—311.
*Achene shape.*—Broad elliptic.
*Flowering season (50% of plants with at least one flower).*—Early (August in Ventura County, Calif.)
*Maturing season (50% of plants with mature fruit.*—Medium (October in Ventura County, Calif.)
*Flowering season.*—Early September to late December (in Ventura County, Calif.).
*Harvest season.*—Early October to late December (in Ventura County, Calif.).
*Harvest maturity.*—Mid-season (November in Ventura County, Calif.).
*Plant hardiness.*—Zone 10 (USDA Plant Hardiness Zone Map).
*Type of bearing.*—Fully remontant (non-flowering runners).

Plant characteristics:
*Average height (cm).*—27.2.
*Average spread (cm).*—33.6.
*Size.*—Ranges from medium to large.
*Habit.*—Semi-upright.
*Density.*—Medium.
*Vigor.*—Strong.

Stolon characteristics:
*Color.*—RHS 146C (yellow green group).
*Anthocyanin coloration.*—RHS 179D (greyed red group).
*Anthocyanin intensity.*—Absent or very weak.
*Pubescence.*—Medium.
*Attitude of hairs.*—Slightly outward.
*Average quantity in nursery (per square foot).*—7 to 8 (medium).
*Average diameter at first bract (mm).*—3.7 (ranges from medium to thick).
*Length from mother plant to first daughter (cm).*—30.2.

Terminal leaflet characteristics:
*Average length (cm).*—7.7.
*Average width (cm).*—6.8.
*Average area terminal ($cm^2$).*—52.0.
*Average length/width ratio.*—1.13 (longer than broad).
*Shape of base.*—Obtuse.
*Shape of apex.*—Obtuse.
*Margins (shape of teeth).*—Obtuse (serrate to crenate).
*Average serrations per leaf.*—20.0.

Foliage characteristics:
*Color of upper surface.*—RHS N137C (medium green).
*Color of lower surface.*—RHS 147C (yellow green group).
*Color of venation, upper surface.*—RHS N137C (green group).
*Color of venation, lower surface.*—RHS 147D (yellow green group).
*Number of leaflets.*—3.
*Leaf size.*—Ranges from medium to small.
*Average length (cm).*—11.5.
*Average width (cm).*—14.1.
*Average area foliage ($cm^2$).*—163.0.
*Shape in cross section.*—Strongly to slightly concave.
*Interveinal blistering.*—Ranges from medium to strong.
*Texture of upper surface (pubescence).*—Medium.
*Texture of lower surface (pubescence).*—Smooth.
*Venation pattern.*—Ranges from pinnate to cross venulate.
*Leaf glossiness.*—Medium.
*Leaf variegation.*—Absent.

Petiole characteristics:
*Petiole color.*—RHS 146C (yellow green group).
*Petiole average length (cm).*—18.8.
*Petiole average diameter (mm).*—3.6.
*Attitude of hairs.*—Slightly outward.
*Frequency of bract leaflets.*—52% occurrence (occasional).
*Size of bract leaflets.*—Ranges from medium to large.
*Pubescence.*—Ranges from moderate to sparse.
*Petiolule color.*—RHS 146C (yellow green group).
*Petiolule average length (mm).*—13.1.
*Petiolule average diameter (mm).*—1.9.

Stipule characteristics:
*Color.*—RHS 146C (yellow green group).
*Anthocyanin coloration.*—N/A.
*Anthocyanin intensity.*—Absent or very weak.
*Average length (mm).*—17.0.
*Average width (mm).*—8.0.
*Shape.*—Triangular.
*Texture (pubescence).*—Medium.
*Shape of base.*—N/A.
*Shape of apex.*—Acute.
*Margins.*—Entire (smooth).

Fruiting truss characteristics:
*Anthocyanin coloration.*—N/A.
*Anthocyanin intensity.*—Absent or very weak.
*Average length at maturity (cm).*—27.2.
*Position relative to foliage.*—Level with.
*Flower quantity (season average per plant).*—18.2 (medium).
*Attitude at first pick.*—Prostrate.
*Pedicel attitude of hairs.*—Slightly outward.
*Pedicel texture (pubescence).*—Medium.

Flower characteristics:
*Petal color, upper surface.*—RHS NN155C (white group).
*Petal color, lower surface.*—RHS NN155C (white group).
*Petal average length (mm).*—10.9.
*Petal average width (mm).*—10.5.
*Petal average length/width ratio.*—1.04 (as long as broad).
*Average petal quantity per flower.*—6.3.
*Petal shape.*—Obovate.
*Petal texture, upper surface.*—Smooth.
*Petal texture, lower surface.*—Smooth.
*Petal shape of base.*—Acute.
*Petal shape of apex.*—Rotund.
*Petal margins.*—Entire (smooth).
*Sepal color, upper surface.*—RHS 137A (green group).
*Sepal color, lower surface.*—RHS 138B (yellow green group).
*Sepal average length (mm).*—12.2.

*Sepal average width* (*mm*).—4.6.
*Sepal average length/width ratio.*—2.65.
*Average sepal quantity per flower.*—12.3.
*Sepal shape* (*outer*).—Ovate.
*Sepal texture, upper surface.*—Light.
*Sepal texture, lower surface.*—Light.
*Sepal shape of apex.*—Acute.
*Sepal margins.*—Ranges from entire (smooth) to acute (serrate).
*Flower bud color.*—RHS 145A (yellow green group).
*Flower bud shape.*—Bell.
*Flower bud average length* (*mm*).—14.2.
*Flower bud average diameter* (*mm*).—7.4.
*Corolla average diameter* (*mm*).—28.2 (medium).
*Flower average depth* (*mm*).—10.1 (medium).
*Calyx average diameter* (*mm*).—31.3.
*Size of calyx relative to corolla.*—Larger.
*Relative position of petals* (*flowers with* 5 *or* 6 *petals*).—Ranges from free to touching.
*Size of inner calyx relative to outer calyx.*—Same.

Reproductive organs:
*Anther color.*—RHS 14A (yellow orange group).
*Filament color.*—RHS 145C (yellow green group).
*Filament average length* (*mm*).—2.6.
*Anther average length* (*mm*).—1.5.
*Anther average width* (*mm*).—1.1.
*Anther shape.*—Broad elliptic.
*Pollen amount.*—Abundant.
*Ovary color.*—RHS 147C (green group).
*Style color.*—RHS 151C (yellow green group).
*Pistil average quantity per flower.*—311.
*Pistil average length* (*mm*).—1.1.
*Style average length* (*mm*).—1.0.
*Stigma average diameter* (*mm*).—0.2.
*Stigma shape.*—Rounded.

Disease and pest reactions:
*Powdery mildew* (*Sphaerotheca macularis*).—Moderately susceptible.
*Angular leaf spot* (*Xanthomonas fragariae*).—Moderate.
*Botrytis fruit rot* (*Botrytis cinerea*).—Moderately susceptible.
*Fusarium wilt* (*Fusarium oxysporum*).—Resistant.
*Anthracnose crown rot* (*Colletotrichum fragariae*).—Susceptible.
*Macrophomina* (*Macrophomina phaseolina*).—Moderate.
*Two-spotted spider mite* (*Tetranychus urticae*).—Moderately susceptible.

We claim:

1. A new and distinct strawberry plant named 'PEP-12.6010', as herein described and illustrated by the characteristics set forth above.

* * * * *